United States Patent [19]

Saville

[11] Patent Number: Plant 5,967

[45] Date of Patent: May 5, 1987

[54] ROSE PLANT NAMED SAVASACH

[75] Inventor: F. Harmon Saville, Rowley, Mass.

[73] Assignee: Nor'East Miniature Roses, Inc., Rowley, Mass.

[21] Appl. No.: 775,038

[22] Filed: Sep. 11, 1985

[51] Int. Cl.[4] ..... A01H 5/00

[52] U.S. Cl. ..... Plt./9

[58] Field of Search ..... Plt./9

*Primary Examiner*—Robert E. Bagwill

*Attorney, Agent, or Firm*—Vincent G. Gioia

[57] ABSTRACT

A new miniature rose variety of Spinel red flower coloring and good exhibition form.

1 Drawing Figure

1

The present invention relates to a new and distinct variety of rose plant of the miniature rose class, which was originated by my crossing as seed parent an unnamed, unpatented seedling of my creation and as pollen parent the rose known as "Shocking Blue" (U.S. Plant Pat. No. 3,846). The varietal denomination of this new variety is "Savasach".

Among the novel characteristics possessed by this new variety which distinguish it from its parents and all other varieties of which I am aware are its unusual Spinel red flowers having deep yellow centers in the open bloom stage that open well from red colored, urn-shaped buds. Asexual reproduction by budding of the new variety as performed in Essex County, Mass., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "53C" is plate 53C of the Royal Horticultural Society Colour Chart.

Parentage: Seedling.

*Seed parent.*—Unnamed, unpatented seedling.

*Pollen parent.*—"Shocking Blue".

Class: Miniature.

The following observations are made of specimens grown outdoors in Essex County, Mass., during the month of May.

FLOWER

Blooming habit: Recurrent.

A. Bud:

(1) *Size.*—Small.

(2) *Form.*—Ovate, pointed.

(3) *Color.*—When sepals first divide — bud color is cardinal red, near 53C. When petals begin to unfurl — near 53A with lighter reverse, near 53C.

(4) *Sepals.*—Longer than bud, slightly foliated.

2

(5) *Peduncle.*—Length — about 1 to $1\frac{1}{4}''$. Aspect — straight. Strength — erect. Color — grass green.

B. Bloom:

(1) *Size.*—Average size when fully expanded — about $1\frac{1}{2}$ to 2 inches.

(2) *Borne.*—Singly and small sprays.

(3) *Form.*—Urn shaped becoming flat, outer petals roll under upon opening.

(4) *Petalage.*—Number of petals under normal conditions — about 35.

(5) *Color.*—After sepals fall, visible bud coloring is cardinal red but upon opening petal top surface coloring is spinel red, near 54C to 54D. Inner petal shading tends to darker tones. Some inner petals have central white streaks. Yellow colored pollen (near 22B) is very conspicuous in open bloom. General tonality from a distance is spinel red with yellow centers. Color at point of petal attachment is near 157D.

C. Petals:

(1) *Texture.*—Moderately thick.

(2) *Appearance.*—Inside — velvety. Outside — satiny.

(3) *Form.*—Wedge shaped, some apex pointed, outer petals reflex pointed, many inner petals roll under at edges.

(4) *Arrangement.*—Regularly arranged, imbricated.

(5) *Petaloids in center.*—Few.

(6) *Persistence.*—Drop off cleanly.

(7) *Fragrance.*—Slight.

(8) *Lasting quality.*—Long lasting on plant.

REPRODUCTIVE ORGANS

A. Stamens, filaments and anthers:

(1) *Arrangement.*—Regular arrangement around styles.

(2) *Color.*—Near 16A.

B. Pollen:

*Color.*—near 22B.

C. Styles: Short, even length.

D. Stigmas:

*Color.*—Near 2D and 53C.

E. Hips: None observed.

PLANT

A. Form: Upright, spreading.

B. Growth: Very vigorous, uniform branching.

*Height attained.*—About 14 to 18 inches.

C. Foliage: Compound 5 to 7 leaflets.

(1) *Size.*—Medium.

(2) *Quantity.*—Abundant.

(3) *Color.*—New foliage: Upper side — near to 137A. Under side — near to 138B. old foliage: Upper side — near 147A. Under side — near 147B.

(4) *Shape.*—Oval, pointed.

(5) *Texture.*—Upper side is glossy and under side is matte.

(6) *Edge.*—Serrated.

(7) *Serration.*—Serrate.

(8) *Leaf stem.*—Color — near 137C. Under side — near 144C.

(9) *Stipules.*—Medium.

(10) *Resistance to disease.*—Black spot — average. Mildew — average. Rust — average.

D. Wood:

(1) *New wood.*—Color — near 143B. Bark — smooth.

(2) *Old wood.*—Color — near 139B. Bark — smooth.

E. Thorns:

(1) *Thorns.*—Quantity (main stalk) — few. On laterals from stalk — none. Form — straight, long pointed, angled slightly downward. Length — medium. Color — near 186C. Position — irregular.

(2) *Prickles.*—Few.

F. Winter hardiness: Requires ordinary protection in extreme climates.

I claim:

1. A new and distinct variety of rose plant of the miniature rose class, substantially as shown and described, characterized particularly by unusual spinel red flowers having dark yellow centers in the open bloom stage.

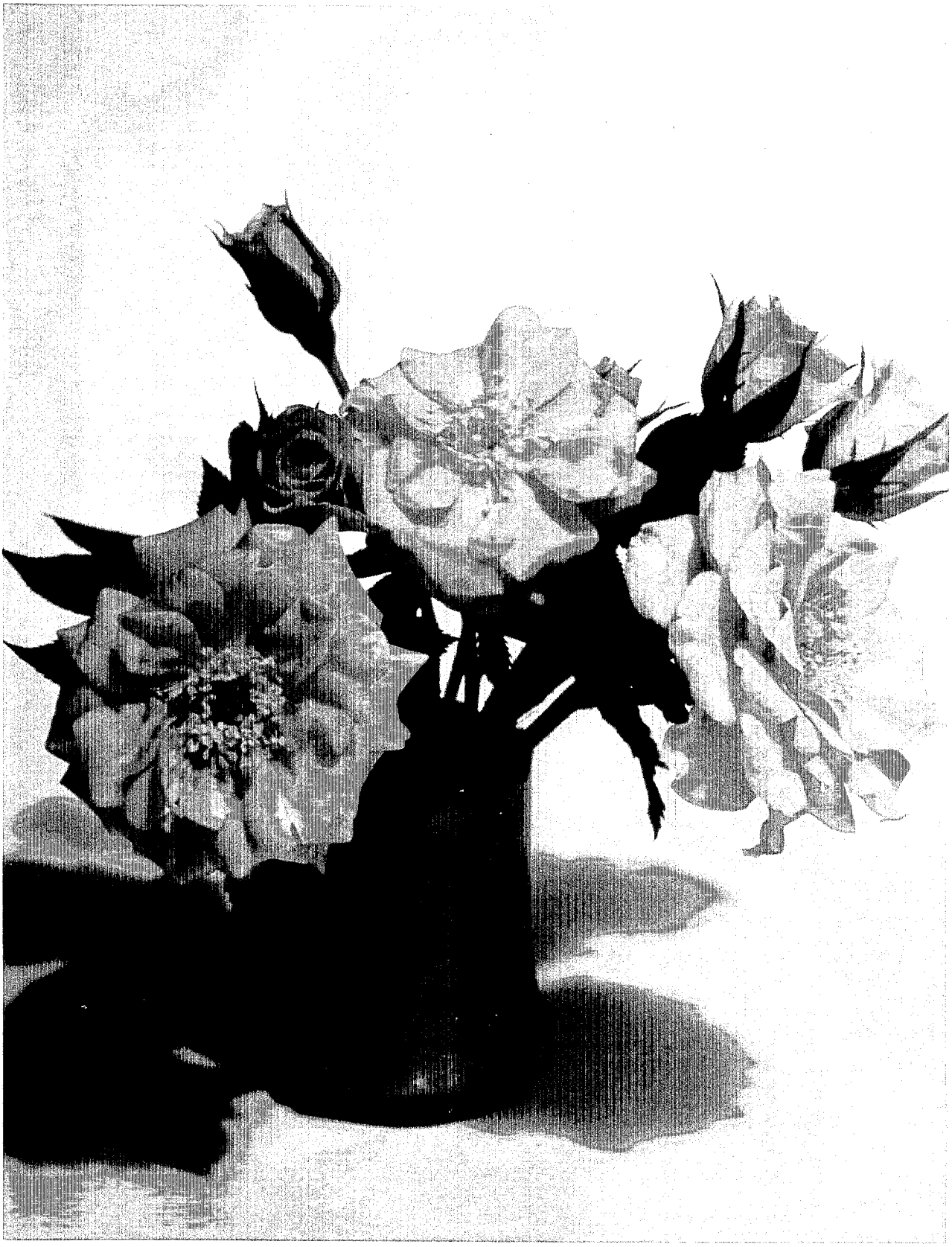

* * * * *